(12) United States Patent
Borchert et al.

(10) Patent No.: US 6,399,816 B1
(45) Date of Patent: Jun. 4, 2002

(54) METHOD FOR SELECTIVELY PRODUCING ACETIC ACID THROUGH THE CATALYTIC OXIDATION OF ETHANE

(75) Inventors: Holger Borchert, Weinstrasse; Uwe Dingerdissen, Seeheim-Jugenheim, both of (DE)

(73) Assignee: Celanese Chemicals Europe GmbH (DE)

(*) Notice: Subject to any disclaimer, the term of this patent is extended or adjusted under 35 U.S.C. 154(b) by 0 days.

(21) Appl. No.: 09/529,666

(22) PCT Filed: Oct. 9, 1998

(86) PCT No.: PCT/EP98/06414

§ 371 (c)(1),
(2), (4) Date: Jun. 5, 2000

(87) PCT Pub. No.: WO99/20592

PCT Pub. Date: Apr. 29, 1999

(30) Foreign Application Priority Data

Oct. 17, 1997 (DE) .......................... 197 45 902

(51) Int. Cl.$^7$ .......................... C07C 21/10; C07C 53/00; C07C 51/16
(52) U.S. Cl. .................... 562/512.2; 562/536; 562/547; 562/548
(58) Field of Search .............................. 562/512.2, 536, 562/547, 548; 502/313, 327, 351

(56) References Cited

U.S. PATENT DOCUMENTS 4,499,301 A    2/1985   Murib
5,162,578 A  * 11/1992   McCain, Jr. et al.
5,260,250 A  * 11/1993   Kitson
5,405,996 A  *  4/1995   Suzuki et al.

FOREIGN PATENT DOCUMENTS

| EP | 0294845 | 12/1988 |
|---|---|---|
| EP | 0620205 | 10/1994 |
| WO | 9805619 | 2/1998 |

* cited by examiner

*Primary Examiner*—Sreeni Padmanabhan
*Assistant Examiner*—Sikarl A. Witherspoon
(74) *Attorney, Agent, or Firm*—Bierman, Muserlian and Lucas

(57) ABSTRACT

The invention relates to a method for selectively producing acetic acid from a gaseous feedstock of ethane, ethylene or mixtures thereof and oxygen at a high temperature. Said gaseous feedstock is brought together with a catalyst containing the elements Mo, Pd, X and Y in the gram-atomic ratios a:b:c:d in combination with oxygen: $Mo_aPd_bX_cY_d$ (I). Symbols X and Y have the following meaning: X represents one or several of the elements chosen from the group Cr, Mn, Nb, Ta, Ti, V, Te and W; Y represents one or several of the elements chosen from the group B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U, the indices a, b, c, d and x represent the gram-atomic ratios of the corresponding elements: a=1, b=0.0001 to 0.01, c=0.4 to 1 and d=0.005 to 1. The space-time yield in the oxidation to acetic acid using the inventive method is >150 kg/hm$^3$. The selectivity of the oxidation reaction of ethane and/or ethylene to acetic acid is especially ≧70 mol %.

10 Claims, No Drawings

METHOD FOR SELECTIVELY PRODUCING ACETIC ACID THROUGH THE CATALYTIC OXIDATION OF ETHANE

This application is a 371 of PCT/EP98/06414 filed Oct. 9, 1998.

The present invention relates to a process for the selective preparation of acetic acid by catalytic gas-phase oxidation of ethane and/or ethylene in the presence of a palladium-containing catalyst.

The oxidative dehydrogenation of ethane to ethylene in the gas phase at temperatures of >500° C. is known, for example, from U.S. Pat. No. 4,250,346, U.S. Pat. No. 4,524,236 and U.S. Pat. No. 4,568,790.

Thus, U.S. Pat. No. 4,250,346 describes the use of a catalyst composition comprising the elements molybdenum, X and Y in a ratio of a:b:c for converting ethane into ethylene, where X is Cr, Mn, Nb, Ta, Ti, V and/or W and Y is Bi, Ce, Co, Cu, Fe, K, Mg, Ni, P, Pb, Sb, Si, Sn, Tl and/or U and a is 1, b is from 0.05 to 1 and c is from 0 to 2. The total value of c for Co, Ni and/or Fe has to be less than 0.5. The reaction is preferably carried out in the presence of added water. The disclosed catalysts can likewise be used for the oxidation of ethane to acetic acid, with the efficiency of the conversion to acetic acid being about 18% at an ethane conversion of 7.5%.

The abovementioned documents are concerned mainly with the preparation of ethylene, less with the targeted preparation of acetic acid.

In contrast, EP-B-0 294 845 describes a process for the selective preparation of acetic acid from ethane, ethylene or mixtures thereof using oxygen in the presence of a catalyst mixture comprising at least A.) a calcined catalyst of the formula $Mo_xV_y$ or $Mo_xV_yZ_y$, where Z may be one or more of the metals Li, Na, Be, Mg, Ca, Sr, Ba, Zn, Cd, Hg, Sc, Y, La, Ce, Al, Tl, Ti, Zr, Hf, Pb, Nb, Ta, As, Sb, Bi, Cr, W, U, Te, Fe, Co and Ni and x is from 0.5 to 0.9, y is from 0.1 to 0.4 and z is from 0.001 to 1, and B.) an ethylene hydration catalyst and/or ethylene oxidation catalyst. The second catalyst component B is, in particular, a molecular sieve catalyst or a palladium-containing oxidation catalyst. When using the catalyst mixture described and passing a gas mixture comprising ethane, oxygen, nitrogen and water vapor through the reactor containing the catalyst, the maximum selectivity is 27% at an ethane conversion of 7%. According to EP 0 294 845, the high conversions of ethane are achieved only using the catalyst mixture described, but not using a single catalyst comprising the components A and B.

A further process for preparing a product comprising ethylene and/or acetic acid is described in EP-B-0 407 091. Here, ethane and/or ethylene and a gas comprising molecular oxygen is brought into contact with a catalyst composition comprising the elements A, X and Y at elevated temperature. A is $Mo_dRe_eW_f$, X is Cr, Mn, Nb, Ta, Ti, V and/or W and Y is Bi, Ce, Co, Cu, Fe, K, Mg, Ni, P, Pb, Sb, Si, Sn, Tl and/or U. The maximum selectivities which can be achieved when using the catalyst described in the oxidation of ethane to acetic acid are 78%. Further by-products formed are carbon dioxide, carbon monoxide and ethylene.

The German Patent Application P 19630832.1, which is not a prior publication, describes a process for the selective preparation of acetic acid from a gaseous feed comprising ethane, ethylene or mixtures thereof plus oxygen at elevated temperature. The feed is brought into contact with a catalyst comprising the elements Mo, Pd, X and Y in combination with oxygen.

Here, X is one or more elements selected from the group consisting of Cr, Mn, Nb, Ta, Ti, V, Te and W and Y is one or more elements selected from the group consisting of B, Al, Ga, In Pt, Zn, Cd, Bi, Ce, Co, Rh, Ir, Cu, Ag, Au, Fe, Ru, Os, K, Rb, Cs, Mg, Ca, Sr, Ba, Zr, Hf, Ni, P, Pb, Sb, Si, Sn, Tl and U.

The gram atom ratios of the corresponding elements are given as follows:

a(Mo)=1; b(Pd)>0; c(X)>0; and d(Y)=0–2.

The catalysts described in the abovementioned application give a maximum space-time yield of 149 kg/hm³ at an acetic acid selectivity of >60 mol %. Space-time yields characterize the amount of acetic acid produced per unit time and catalyst volume. Higher space-time yields are desirable since the size of the reactors and the amount of circulated gas can be reduced thereby.

It is therefore an object of the invention to provide a process which allows ethane and/or ethylene to be oxidized to acetic acid in a simple and targeted manner and at high selectivity and space-time yield under reaction conditions which are as mild as possible.

It has surprisingly been found that it is possible to oxidize ethane and/or ethylene to acetic acid under relatively mild conditions in a simple manner at high selectivity and excellent space-time yields when using a catalyst comprising the elements molybdenum and palladium and one or more elements selected from the group consisting of chromium, manganese, niobium, tantalum, titanium, vanadium, tellurium and/or tungsten.

The present invention accordingly provides a process for the selective preparation of acetic acid from a gaseous feed comprising ethane, ethylene or mixtures thereof plus oxygen at elevated temperature, wherein the gaseous feed is brought into contact with a catalyst comprising the elements Mo, Pd, X and Y in the gram atom ratios a:b:c:d in combination with oxygen

$$Mo_aPd_bX_cY_d \qquad (I)$$

where the symbols X and Y have the following meanings:
X is one or more elements selected from the group consisting of: Cr, Mn, Ta, Ti, V, Te and W, in particular V and W;
Y is one or more elements selected from the group consisting of: B, Al, Ga, In, Pt, Zn, Cd, Bi, Ce, Co, Cu, Rh, Ir, Au, Ag, Fe, Ru, Os, K, Rb, Cs, Mg, Ca, Sr, Ba, Nb, Zr, Hf, Ni, P, Pb, Sb, Si, Sn, Tl and U, in particular Nb, Ca, Sb and Li.

The indices a, b, c and d are the gram atom ratios of the corresponding elements, where a=1,
b=0.0001–0.01,
c=0.4–1 and
d=0.005–1.

If X and Y represent a plurality of different elements, the indices c and d can likewise assume a plurality of different values.

Furthermore, the present invention provides a catalyst for the selective preparation of acetic acid comprising the elements Mo, Pd, X and Y in the gram atom ratios a:b:c:d in combination with oxygen.

The gram atom ratios a:b:c:d are preferably within the following ranges:

a=1;
b=0.0001–0.005;
c=0.5–0.8 and
d=0.01–0.3.

Palladium contents in the catalyst which are above the upper limit indicated promote carbon dioxide formation in the process of the invention. Furthermore, higher palladium contents are generally also avoided because they make the catalyst unnecessarily expensive. On the other hand, palladium contents below the limit indicated favor formation of ethylene.

Apart from the elements molybdenum and palladium, the catalyst used according to the invention preferably further comprises vanadium, niobium, antimony and calcium in combination with oxygen. The gram atom ratios $a:b:c^1:d^1:d^2:d^3$ of the elements Mo:Pd:V:Nb:Sb:Ca are preferably as follows:

a (Mo)=1;
b (Pd)=0.0001–0.005, in particular 0.0001–0.001;
$c^1$ (V)=0.4–1.0;
$d^1$ (Nb)=0.01–0.2;
$d^2$ (Sb)=0.01–0.3;
$d^3$ (Ca)=0.01–0.3.

Examples of such catalyst compositions which are preferably used in the process of the invention are:

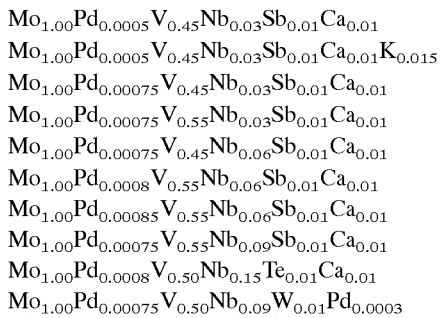

$Mo_{1.00}Pd_{0.0005}V_{0.45}Nb_{0.03}Sb_{0.01}Ca_{0.01}$
$Mo_{1.00}Pd_{0.0005}V_{0.45}Nb_{0.03}Sb_{0.01}Ca_{0.01}K_{0.015}$
$Mo_{1.00}Pd_{0.00075}V_{0.45}Nb_{0.03}Sb_{0.01}Ca_{0.01}$
$Mo_{1.00}Pd_{0.00075}V_{0.55}Nb_{0.03}Sb_{0.01}Ca_{0.01}$
$Mo_{1.00}Pd_{0.00075}V_{0.45}Nb_{0.06}Sb_{0.01}Ca_{0.01}$
$Mo_{1.00}Pd_{0.0008}V_{0.55}Nb_{0.06}Sb_{0.01}Ca_{0.01}$
$Mo_{1.00}Pd_{0.00085}V_{0.55}Nb_{0.06}Sb_{0.01}Ca_{0.01}$
$Mo_{1.00}Pd_{0.00075}V_{0.55}Nb_{0.09}Sb_{0.01}Ca_{0.01}$
$Mo_{1.00}Pd_{0.0008}V_{0.50}Nb_{0.15}Te_{0.01}Ca_{0.01}$
$Mo_{1.00}Pd_{0.00075}V_{0.50}Nb_{0.09}W_{0.01}Pd_{0.0003}$

The catalysts used according to the invention can be prepared by conventional methods. These start from a slurry, in particular an aqueous solution, comprising the individual starting components of the elements in the appropriate proportions.

The starting materials of the individual components for preparing the catalyst of the invention are, apart from the oxides, preferably water-soluble substances such as ammonium salts, nitrates, sulfates, halides, hydroxides and salts of organic acids which can be converted into the corresponding oxides by heating. To mix the components, aqueous solutions or suspensions of the metal salts are prepared and mixed.

In the case of molybdenum, it is advisable to use the corresponding molybdates, e.g. ammonium molybdate, as starting compounds because of their commercial availability.

Suitable palladium compounds are, for example, palladium(II) chloride, palladium(II) sulfate, tetramminepalladium(II) nitrate, palladium(II) nitrate and palladium(II) acetylacetonate.

The reaction mixture obtained is then stirred at from 50 to 100° C. for from 5 minutes to 5 hours. The water is subsequently removed and the catalyst which remains is dried at a temperature of from 50 to 150° C., in particular from 80 to 120° C.

If the resulting catalyst is subsequently subjected to a further calcination process, it is advisable to calcine the dried and pulverized catalyst at a temperature in the range from 100 to 800° C., in particular from 200 to 500° C., in the presence of nitrogen, oxygen or an oxygen-containing gas. The time is from 2 to 24 hours.

The catalyst can be used without a support material or can be mixed with or applied to an appropriate support material. Suitable support materials are customary support materials such as porous silicon dioxide, ignited silicon dioxide, kieselguhr, silica gel, porous or nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride or silicon carbide or else glass, carbon fiber, metal oxide or metal meshes or corresponding monoliths.

Preferred support materials have a surface area of less than 100 m²/g. Preferred support materials are silicon dioxide and aluminum oxide having a low specific surface area. The catalyst can be used as a heterogeneous oxidation catalyst after shaping as regularly or irregularly shaped support bodies or else in powder form.

The reaction can be carried out in a fluidized bed or in a fixed-bed reactor. For use in a fluidized bed, the catalyst is milled to a particle size in the ranqe from 10 to 200 $\mu$m.

The gaseous feed comprises ethane and/or ethylene which are fed to the reactor as pure gases or in admixture with one or more other gases. Examples of such additional or carrier gases are nitrogen, methane, carbon monoxide, carbon dioxide, air and/or water vapor. The gas comprising molecular oxygen can be air or a gas comprising more or less molecular oxygen than air, e.g. oxygen. The proportion of water vapor can be in the range from 0 to 50% by volume. Higher water vapor concentrations would make the work-up of the aqueous acetic acid formed unnecessarily expensive for process reasons. The ratio of ethane/ethylene to oxygen is advantageously in the range from 1:1 to 10:1, preferably from 2:1 to 8:1. Relatively high oxygen contents are preferred since the achievable ethane conversion and thus the yield of acetic acid is higher. Oxygen or the gas comprising molecular oxygen is preferably added in a concentration range outside the explosive limtis under the reaction conditions since this makes the process easier to carry out. However, it is also possible to employ an ethane/ethylene to oxygen ratio within the explosive limits.

The reaction is carried out at temperatures of from 200 to 500° C., preferably from 200 to 400° C. The pressure can be atmospheric or superatmospheric, e.g. in the range from 1 to 50 bar, preferably from 1 to 30 bar.

The reaction can be carried out in a fixed-bed or fluidized-bed reactor.

Advantageously, ethane is first mixed with the inert gases such as nitrogen or water vapor before oxygen or the gas comprising molecular oxygen is fed in. The mixed gases are preferably preheated to the reaction temperature in a preheating zone before the gas mixture is brought into contact with the catalyst. Acetic acid is separated from the gas leaving the reactor by condensation. The remaining gases are recirculated to the reactor inlet where oxygen or the gas comprising molecular oxygen and also ethane and/or ethylene are metered in.

On comparing the catalysts of the invention with those of the prior art, it is found that the present catalysts achieve higher space-time yields and acetic acid selectivities under identical reaction conditions (reaction feed gas, pressure, temperature).

When using the catalyst of the invention, the selectivity in the oxidation of ethane and/or ethylene to acetic acid is $\geq 70$ mol %, preferably $\geq 80$ mol %, in particular $\geq 90$ mol %, and the space-time yield is >150 kg/hm³, in particular >200 kg/hm³, preferably >300 kg/hm³, so that the process of the invention enables, in comparison with the prior art, an increase in the acetic acid yields to be achieved in a simple manner while simultaneously reducing the formation of undesired by-products.

EXAMPLES

The catalyst composition described in the examples is given in relative atom ratios.

Catalyst Ppreparation

Catalyst (I):

A catalyst having the following composition was prepared:

$Mo_{1.00}Pd_{0.00075}V_{0.45}Nb_{0.03}Sb_{0.01}Ca_{0.01}$

Solution 1:
40 g of ammonium molybdate in 100 ml of water
Solution 2:
12.0 g of ammonium metavanadate in 200 ml of water
Solution 3:
4.19 g of niobium oxalate, 0.96 g of antimony oxalate, 0.68 g of calcium nitrate in 100 ml of water
Solution 4:
0.039 g of palladium acetate in 100 ml of acetone.

The aqueous solutions 1 to 3 are stirred separately at 70° C. for 15 minutes. The third is then added to the second. The combined mixtures are stirred at 70° C. for 15 minutes before these are added to the first. Solution 4 is then added thereto. The resulting mixture is stirred at 70° C. for 15 minutes and subsequently evaporated to a volume of 400 ml of solution. The mixture is spray-dried and calcined in stationary air at 120° C. for 2 hours and 300° C. for 5 hours. The catalyst is then lightly ground in a mortar and pressed into pellets. These are crushed on a sieve to give a sieve fraction of from 0.35 to 0.7 mm.

Catalyst (II):

A catalyst having the following composition was prepared:

$Mo_{1.00}Pd_{0.0005}V_{0.45}Nb_{0.03}Sb_{0.01}Ca_{0.01}$

Solution 1:
40 g of ammonium molybdate in 100 ml of water
Solution 2:
12.0 g of ammonium metavanadate in 200 ml of water
Solution 3:
4.19 g of niobium oxalate, 0.96 g of antimony oxalate, 0.68 g of calcium nitrate in 100 ml of water
Solution 4:
0.026 g of palladium acetate in 100 ml of acetone.

The Peparation of the Catalyst was Carried out as Described in Catalyst Example (I).

Catalyst (III):

A catalyst having the following composition was prepared:

$Mo_{1.00}Pd_{0.00085}V_{0.55}Nb_{0.06}Sb_{0.01}Ca_{0.01}$

Solution 1:
40 g of ammonium molybdate in 100 ml of water
Solution 2:
14.7 g of ammonium metavanadate in 200 ml of water
Solution 3:
8.38 g of niobium oxalate, 0.96 g of antimony oxalate, 0.68 g of calcium nitrate in 100 ml of water
Solution 4:
0.044 g of palladium acetate in 100 ml of acetone.

The Preparation of the Catalyst was Carried out as Described in Catalyst Example (I).

Catalyst (IV):

A catalyst having the following composition was prepared:

$Mo_{1.00}Pd_{0.00075}V_{0.55}Nb_{0.09}Sb_{0.01}Ca_{0.01}$

Solution 1:
40 g of ammonium molybdate in 100 ml of water
Solution 2:
14.7 g of ammonium metavanadate in 200 ml of water
Solution 3:
12.75 g of niobium oxalate, 0.96 g of antimony oxalate, 0.68 g of calcium nitrate in 100 ml of water.
Solution 4:
0.039 g of palladium acetate in 100 ml of acetone.

The Preparation of the Catalyst was Carried out as Described in Catalyst Example (I).

Catalyst (V):

A catalyst having the following composition was prepared:

$Mo_{1.00}Pd_{0.00085}V_{0.55}Nb_{0.09}Sb_{0.01}Ca_{0.01}$

Solution 1:
40 g of ammonium molybdate in 100 ml of water
Solution 2:
14.7 g of ammonium metavanadate in 200 ml of water
Solution 3:
12.75 g of niobium oxalate, 0.96 g of antimony oxalate, 0.68 g of calcium nitrate in 100 ml of water
Solution 4:
0.044 g of palladium acetate in 100 ml of acetone.

The Preparation of the Catalyst was Carried out as Described in Catalyst Example (I).

Comparative Example

Catalyst (VI)

Catalyst Example (I) from the German Patent Application P 19630832.1, which is not a prior publication, having the composition $Mo_{1.00}Pd_{0.0005}V_{0.25}Nb_{0.12}$ was prepared in order to demonstrate the higher space-time yield of the catalysts of the invention.

Solution 1:
61.75 g of ammonium molybdate and 0.039 g of palladium acetate in 200 ml of water
Solution 2:
10.22 g of ammonium metavanadate in 250 ml of water.
Solution 3:
27.51 g of niobium oxalate in 25 ml of water.

The solutions are stirred separately at 90° C. for 15 minutes. The third solution is then added to the second. The combined mixtures are stirred at 90° C. for 15 minutes before the first solution is added thereto. The resulting mixture is stirred at 90° C. for 15 minutes. The mixture is subsequently spray-dried and calcined in stationary air at 120° C. for 2 hours and 300° C. for 5 hours. The catalyst is then lightly ground in a mortar and pressed into pellets. These are crushed on a sieve to give a sieve fraction of from 0.35 to 0.7 mm.

Method of Catalyst Testing

A steel reactor having an internal diameter of 10 mm was charged with 5 or 10 ml of the catalyst. The catalyst was heated to 250° C. in a stream of air. The pressure was subsequently adjusted by means of an admission pressure regulator. The desired ethane:oxygen:nitrogen mixture was fed together with water into a vaporizer zone where water was vaporized and mixed with the gases. The reaction temperature was measured by means of a thermocouple in the catalyst bed. The reaction gas was analyzed on-line by gas chromatography.

In the examples, the following terms are defined as:

Ethane conversion (%)=100×([CO]/2+[CO$_2$]/2+[C$_2$H$_4$]+[CH$_3$COOH])/([CO]/2+[CO$_2$]/2+[C$_2$H$_2$]+[C$_2$H$_6$]+[CH$_3$COOH])

Ethylene selectivity (%)=100×([C$_2$H$_4$])/([CO]/2+[CO$_2$]/2+[C$_2$H$_4$]+[CH$_3$COOH])

Acetic acid selectivity (%)=100×([CH$_3$COOH])/([CO]/2+[CO$_2$]/2+[C$_2$H$_4$]+[CH$_3$COOH])

where

[ ]=concentrations in mol % and

[C$_2$H$_6$]=concentration of the unreacted ethane.

The residence time is defined as:

t (s)=bed volume of the catalyst (ml)/volume flow of the gas through the reactor based on the reaction conditions (ml/s)

Reaction procedure

The reactor inlet gas consisted of 40% by volume of ethane, 8% by volume of oxygen, 32% by volume of nitrogen and 20% by volume of water vapor. Since the space-time yield is dependent on the reaction pressure, all comparative examples were carried out at 15 bar for reasons of comparability. Reaction conditions and results are summarized in the following table.

Compared to the comparative catalyst (VI), significantly higher selectivities and space-time yields for acetic acid are achieved using the catalysts (I) to (V) at the same temperatures.

TABLE 1

| Ex. | Catalyst | Temperature (° C.) | Pressure (bar) | Residence time(s) | Ethane conversion (%) | Acetic acid selectivity (%) | Ethylene selectivity (%) | Space-time yield [kg/hm$^3$] | CO + CO$_2$ selectivity (%) |
|---|---|---|---|---|---|---|---|---|---|
| 1 | (I) | 300 | 15 | 14 | 15 | 63 | 25 | 184 | 11 |
| 2 | (II) | 300 | 15 | 14 | 15 | 69 | 19 | 193 | 12 |
| 3 | (III) | 300 | 15 | 10 | 10 | 86 | 2 | 247 | 12 |
| 4 | (IV) | 280 | 15 | 15 | 14 | 91 | 1 | 215 | 8 |
| 5 | (IV) | 300 | 15 | 10 | 14 | 89 | 3 | 355 | 8 |
| 6 | (IV) | 300 | 15 | 7 | 13 | 81 | 11 | 410 | 8 |
| 7 | (IV) | 310 | 15 | 7 | 15 | 85 | 3 | 470 | 12 |
| 8 | (V) | 300 | 15 | 10 | 15 | 77 | 14 | 325 | 9 |
| 9 | (VI) | 280 | 15 | 30 | 15 | 77 | 2 | 72 | 21 |

Experimental Report

| Catalyst composition | Temperature (° C.) | Pressure (bar) | Residence time(s) | Ethane conversion (%) | Acetic acid select. (%) | Ethylene select. (%) | Space-time yield (kg/hm$^3$) | CO-CO$_2$ select. (%) |
|---|---|---|---|---|---|---|---|---|
| Mo$_{1.0}$V$_{0.55}$Nb$_{0.09}$Bi$_{0.03}$Sb$_{0.01}$Ca$_{0.01}$Pd$_{0.00075}$ | 280 | 15 | 14.8 | 11.2 | 85.2 | 2.1 | 182 | 12.7 |
| Mo$_{1.0}$V$_{0.55}$Nb$_{0.09}$Bi$_{0.03}$Sb$_{0.01}$Ca$_{0.01}$Pd$_{0.00075}$ | 280 | 15 | 7.4 | 6.4 | 76.9 | 6.3 | 187 | 16.8 |
| Mo$_{1.0}$V$_{0.55}$Nb$_{0.09}$Bi$_{0.03}$Sb$_{0.01}$Ca$_{0.01}$Pd$_{0.00075}$ | 300 | 15 | 14.3 | 14.3 | 66.2 | 20.7 | 181 | 13.1 |
| Mo$_{1.0}$V$_{0.55}$Nb$_{0.09}$Bi$_{0.03}$Sb$_{0.01}$Ca$_{0.01}$Pd$_{0.00075}$ | 300 | 15 | 7.1 | 10.6 | 47.9 | 37.6 | 193 | 14.5 |
| Mo$_{1.0}$V$_{0.55}$Nb$_{0.09}$Sb$_{0.03}$Ca$_{0.01}$Pd$_{0.00075}$Au$_{0.00028}$ | 300 | 15 | 7.4 | 7.3 | 62.9 | 6.1 | 174 | 31.0 |
| Mo$_{0.97}$V$_{0.55}$Nb$_{0.09}$Sb$_{0.01}$Ca$_{0.01}$K$_{0.01}$Pd$_{0.00075}$ | 280 | 15 | 14.8 | 13.1 | 83.0 | 3.2 | 206 | 13.9 |
| Mo$_{0.97}$V$_{0.55}$Nb$_{0.09}$Sb$_{0.01}$Ca$_{0.01}$K$_{0.01}$Pd$_{0.00075}$ | 280 | 15 | 7.4 | 11.2 | 66.4 | 6.0 | 264 | 27.5 |
| Mo$_{0.97}$V$_{0.55}$Nb$_{0.09}$Sb$_{0.01}$Ca$_{0.01}$K$_{0.01}$Pd$_{0.00075}$ | 300 | 15 | 14.3 | 15.0 | 68.9 | 19.2 | 196 | 11.9 |
| Mo$_{0.97}$V$_{0.55}$Nb$_{0.09}$Sb$_{0.01}$Ca$_{0.01}$K$_{0.01}$Pd$_{0.00075}$ | 300 | 15 | 7.1 | 13.6 | 55.7 | 27.1 | 288 | 17.2 |

What is claimed is:

1. A process for the selective preparation of acetic acid from a gaseous feed comprising ethane, or mixtures of ethane and ethylene thereof plus oxygen at elevated temperature, which comprises bringing the gaseous feed into contact with a catalyst comprising the elements Mo, Pd, X and Y in the gram atom ratios a:b:c:d in Combination with oxygen $$Mo_aPd_bX_cY_d \quad (I)$$

where the symbols X and Y have the following meanings:
X is one or more elements selected from the group consisting of Nb, Ta, V, Te and W;
Y is one or more elements selected from the group consisting of Bi, Cu, Ag, Au, Li, K, Rb, Cs, Mg, Ca, Sr, Ba, Nb, Zr, Hf and Sb;
the indices a, b, c, d and x are the gram atom ratios of the corresponding elements, where
a=1; b=0.0001–0.01; c=0.4–1; and d=0.005–1
and the space-time yield in the oxidation to acetic acid is >150 kg/hm³, with the proviso that Mo and the elements X do not derive from a hetero-poly-acid.

2. The process as claimed in claim 1, wherein X and/or Y are a plurality of elements and the indices c and d may assume different values for different elements.

3. The process as claimed in claim 1, wherein the temperature is in the range from 200 to 500° C.

4. The process as claimed in claim 1, wherein the pressure in the reactor is in the range from 1 to 50 bar (1.02–50.95 kg/cm²).

5. The process as claimed in claim 1, wherein b is in the range from 0.0001 to 0.001.

6. The process as claimed in claim 1, wherein ethane mixed with at least one further gas is fed to the reactor.

7. The process as claimed in claim 6, wherein the further gas fed in is nitrogen, oxygen, methane, carbon monoxide, carbon dioxide, ethylene and/or water vapor.

8. The process as claimed in claims 1, wherein the catalyst comprises at least one of the following compositions in combination with oxygen:

$Mo_{1.00}Pd_{0.0005}V_{0.45}Nb_{0.03}Sb_{0.01}Ca_{0.01}$ $Mo_{1.00}Pd_{0.0005}V_{0.45}Nb_{0.03}Sb_{0.01}Ca_{0.01}K_{0.015}$ $Mo_{1.00}Pd_{0.00075}V_{0.45}Nb_{0.03}Sb_{0.01}Ca_{0.01}$ $Mo_{1.00}Pd_{0.00075}V_{0.55}Nb_{0.03}Sb_{0.01}Ca_{0.01}$ $Mo_{1.00}Pd_{0.00075}V_{0.45}Nb_{0.06}Sb_{0.01}Ca_{0.01}$ $Mo_{1.00}Pd_{0.0008}V_{0.55}Nb_{0.06}Sb_{0.01}Ca_{0.01}$ $Mo_{1.00}Pd_{0.00085}V_{0.55}Nb_{0.06}Sb_{0.01}Ca_{0.01}$ $Mo_{1.00}Pd_{0.00075}V_{0.55}Nb_{0.09}Sb_{0.01}Ca_{0.01}$ $Mo_{1.00}Pd_{0.0008}V_{0.15}Te_{0.03}Sb_{0.01}Ca_{0.01}$ $Mo_{1.00}Pd_{0.00075}V_{0.50}Nb_{0.09}W_{0.01}Pd_{0.01}$.

9. The process as claimed in claim 1, wherein the catalyst is mixed with a support material or fixed on a support material.

10. The process as claimed in claim 1, wherein the selectivity of the oxidation reaction of ethane and/or ethylene to acetic acid is ≧70 mol %.

* * * * *